United States Patent [19]

Hagen et al.

[11] Patent Number: 4,807,621

[45] Date of Patent: Feb. 28, 1989

[54] MULTI-ELEMENT FLAT ELECTRODE ESPECIALLY USEFUL FOR HF-SURGERY

[75] Inventors: Uwe Hagen, Forchheim; Udo Redler, Effeltrich, both of Fed. Rep. of Germany

[73] Assignee: Siemens Aktiengesellschaft, Berlin and Munich, Fed. Rep. of Germany

[21] Appl. No.: 97,481

[22] Filed: Sep. 15, 1987

[30] Foreign Application Priority Data

Jun. 3, 1987 [DE] Fed. Rep. of Germany ....... 3718585

[51] Int. Cl.⁴ ............................................. A61B 17/39
[52] U.S. Cl. .................................. 128/303.13; 128/798
[58] Field of Search ....................... 128/303.13, 303.14, 128/303.17, 639, 640, 641, 644, 798, 802, 803, 908

[56] References Cited

U.S. PATENT DOCUMENTS

| 3,683,923 | 8/1972 | Anderson | 128/303.14 |
| 3,720,209 | 3/1973 | Bolduc | 128/798 X |
| 4,082,087 | 4/1987 | Howson | 128/640 |
| 4,381,789 | 5/1983 | Naser et al. | 128/798 |

FOREIGN PATENT DOCUMENTS

| 394385 | 1/1923 | Fed. Rep. of Germany | 128/798 |
| 3623293 | of 0000 | Fed. Rep. of Germany | . |
| 8205363 | 7/1985 | Fed. Rep. of Germany | . |
| 3544443 | 6/1987 | Fed. Rep. of Germany | . |

Primary Examiner—Lee S. Cohen
Attorney, Agent, or Firm—Lawrence C. Edelman

[57] ABSTRACT

An electrode, in a first embodiment, comprises three sub-electrodes which are of essentially triangular shape and form a rectangular contact surface. Preferably, two right-angular sub-electrodes and an acute isosceles sub-electrode lying in-between these are employed. In a second embodiment the electrode comprises three sub-electrodes of essentially rectangular shape. One sub-electrode is preferably formed in a T-shape, and the foot of the T lies between two other rectangular sub-electrodes.

The electrode is preferably used as a neutral electrode in a HF-surgical apparatus. An associated monitoring circuit allows a rapid determination of whether the entire electrode or only a sub-electrode is in good electrical contact with the skin surface of a patient to which the surgical apparatus is being applied.

2 Claims, 1 Drawing Sheet

MULTI-ELEMENT FLAT ELECTRODE ESPECIALLY USEFUL FOR HF-SURGERY

BACKGROUND OF THE INVENTION

1. Field of the Invention

The invention relates to an electrode comprising a minimum of two elements, and especially a neutral electrode in which two sub-electrodes are arranged in juxtaposition in a given direction and have facing edges running at an angle to the given direction.

2. Description of the Prior Art

A neutral electrode of the type described above operating with two flat sub-electrodes is known in the art, for example through German registered utility model 82 05 363 and German patent application No. P 36 23 293.9 (corresponding to U.S. patent application Ser. No. 035,690 filed Apr. 7, 1987 in the name of Feucht et al.).

It has been shown that a multi-element design of a neutral electrode is desirable when it is to be determined, through the use of a monitoring circuit, whether the neutral electrode is making a large surface contact, and not just point contact, with a patient during a surgical procedure. Such a monitoring circuit is described in German patent application No. P 35 44 443.6 having the title "Procedure and Circuit Arrangement for Monitoring the Indifferent Electrode of a HF-Surgical Apparatus for Flat Surface Contact" (corresponding to U.S. patent application Ser. No. 929,561). A monitoring circuit is also known in the art through U.S. Pat. No. 3,683,923.

In the forenoted German patent application No. P 36 23 293.9 it is stated that a simple fabrication of an electrode having a minimum of two elements is possible when the two sub-electrodes exhibit juxtapositioned facing edges that are at an angle to the given direction. In such a construction it is possible to attach connecting leads of equal length to the sub-electrodes. In this way fabrication is simplified. The routing of the conducting leads is also simplified.

It has now been shown that in the design of a multi-element neutral electrode, it is desirable to have a dependable and rapid indication of even a minimal lifting or peeling of a sub-electrode from the under layer or contacting surface at the patient, in order to eliminate harm to the patient. This is not the case, to the desired degree, in the application of essentially rectangular or trapezoidal shaped sub-electrodes and can be improved upon.

The basic object of the invention is therefore the continued improvement of an electrode of the kind referred to above in such a manner that a lifting or peeling may be rapidly and dependably detected through the use of a monitoring circuit.

SUMMARY OF THE INVENTION

This object is realized in accordance with the invention through the provision of three sub-electrodes having an essentially triangular shape.

In accordance with a first embodiment of the invention, provision is made for a triangular sub-electrode to be in symmetrical juxtaposition with two additional triangular electrodes, and an electrical lead connection is provided at the side of the electrode at which the point of the surrounded sub-electrode lies. The two outer sub-electrodes are preferably in the form of right triangles and the middle sub-electrode preferably in the form of an isosceles triangle.

This form of construction is preferred since all three lead connections may then be of equal length; in this way, no asymmetry can result in the three impedances, if all three electrode surfaces are selected to be of equal size.

In accordance with a second embodiment of the invention, provision is made for a central triangular sub-electrode to be symmetrical juxtaposition with two outer additional triangular sub-electrodes, and for an electrical lead connection to be provided on the side of the electrode at which the points of the two outer sub-electrodes lie. In this form of construction the lead connections of the two outer sub-electrodes may be somewhat longer than the lead connection to the middle sub-electrode. Such an asymmetry may however be compensated for in the layout of the monitoring circuit.

The object referred to is also realized in accordance with the invention through the provision of three sub-electrodes of essentially rectangular shape in which two sub-electrodes are in juxtaposition at right angles to the given direction. A third basic design of such kind, has an additional sub-electrode, preferably having a T-shape with its foot lying between the two first named sub-electrodes.

Other features and advantages of the invention will be apparent from the description of the preferred embodiments, and from the claims.

For a fuller understanding of the present invention, reference should now be made to the following detailed description of the preferred embodiments of the invention and to the accompanying drawings.

DETAILED DESCRIPTION OF THE PREFERRED EMBODIMENT

Figure 1:
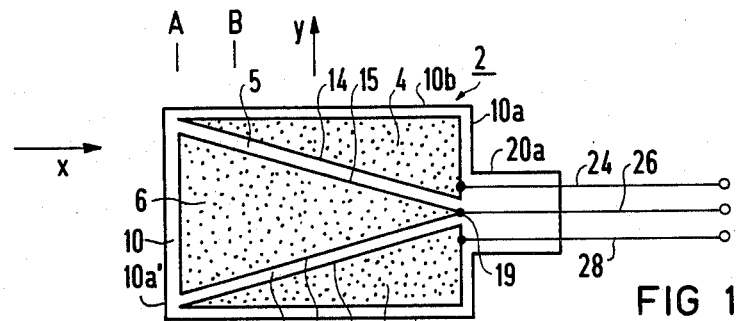
FIG. 1 illustrates a plan view of a three-element neutral electrode for a HF-surgical apparatus.

According to FIG. 1, a neutral electrode 2 for a HF (High Frequency)-surgical apparatus comprises three flat surface sub-electrodes 4, 6 and 8 each two of which are separated by an insulating strip 5 and/or 7 or by a strip of low electrical conductivity. Sub-electrodes 4 and 6 are arranged in juxtaposition in a given direction indicated by arrow x. Correspondingly, sub-electrodes 6 and 8 are arranged in a juxtaposition that is parallel to the x-direction. All three sub-electrodes 4, 6 and 8 are essentially triangular in shape. They are in the form of a metal foil or metal grid and are fastened to a flexible support 10. Support 10, which is preferably designed to be self-adhesive and can be made of rubber, is essentially of rectangular shape. In the present design example, support 10 is longer in the x-direction than the y-direction which is perpendicular to the x-direction. Support 10 extends beyond the boundries of the three sub-electrodes at its outer edges. Its two sides 10a and 10a' are thus somewhat shorter than the sides 10b and 10b', which run parallel to the x-direction.

As may be seen, the three sub-electrodes 4, 6 and 8 are arranged in juxtaposition in the y-direction. They thereby form an essentially rectangular contact surface for the patient. Thus, an arrangement results in which two outer right triangular sub-electrodes 4 and 8 are placed symmetrically and adjacent to a center acute isosceles triangle. The first and second sub-electrodes 4 and 6, respectively, exhibit facing edges 14 and 15 running at an angle to the given x-direction. Edges 14 and 15 run parallel to each other and form an insulating strip 5. Correspondingly, the second and third sub-electrodes 6 and 8 also exhibit facing edges 16 and 17 running at an angle to the given x-direction. Edges 16 and 17 also run parallel to each other and form a second insulating strip 7. Edges 15 and 16 of the middle sub-electrode 6 run at an angle of 20 degrees or more to the x-direction.

An extension or supporting tab for an electrical lead connector 20a is provided on that side 10a of the rectangular support 10, at which a corner point 19 of the middle or enclosed sub-electrode 6 is located. Lead connector 20 picks up three connecting leads 24, 26, and 28 for sub-electrodes 4, 6 and 8, respectively. As may be seen, the three electrical connecting points for leads 24, 26 and 28 are located close together at the sub-electrodes 4, 6 and 8. It is thus possible to make the connecting leads 24, 26 and 28 of equal length, which simplifies fabrication and keeps the cost of spares to a minimum. Moreover no assymetrical impedances determined by the connecting leads 24, 26 and 28 result which may interfere with the related monitoring circuitry (shown e.g. in the forenoted German application No. P 35 44 443.6 or U.S. Pat. No. 3,683,923).

FIG. 1 shows a construction in which the surface area of the middle sub-electrode 6 is formed somewhat larger than the two adjacent sub-electrodes 4 and 8, and in fact about twice as large. However, in some cases, it may be advantageous to form all three sub-electrodes 4, 6 and 8 with equal surface areas.

The electrode 2 shown in FIG. 1 is characterized by the fact that each of the three sub-electrodes has at least one corner point lying on the same line A—A. By this arrangement, a peeling of the sub-electrodes 4, 6 and 8 from the skin surface, for example from the line A—A in the direction of the line B—B, is easily and rapidly detectable. For example, in such a case, the change in the contact surface of the middle sub-electrode 6 would be substantially greater than the change in the contact surface of each of the two adjacent sub-electrodes 4 and 8.

Figure 2:
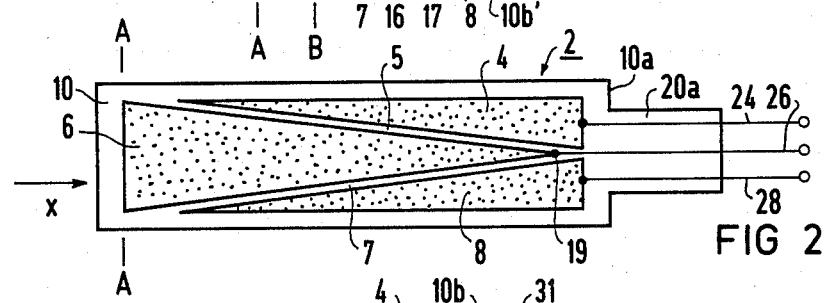
FIG. 2 illustrates a three-element neutral electrode of lengthened form as compared to FIG. 1.

FIG. 2 shows a lengthened construction of an electrode 2. Here only two connecting leads 24 and 28 are of equal length. Furthermore, the corner points of all three sub-electrodes 4, 6 and 8 do not lie on line A—A. Nevertheless, here too there is assurance that a peeling of the electrode 2 from the patient can be easily and rapidly detected.

Figure 3:
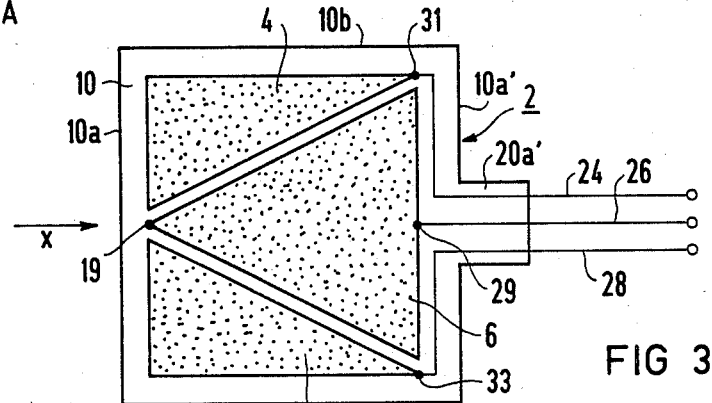
FIG. 3 illustrates a further three-element neutral electrode in which the points of electrical connection are modified in comparison to those of FIGS. 1 and 2.

The construction according to FIG. 3 essentially differs from those of FIGS. 1 and 2 in that a lead connection 20a' is provided on that side 10a' that is opposite the corner point 19 of the middle sub-electrode 6. Thus, here again, two additional right triangular sub-electrodes 4 and 8 are symmetrically located adjacent to an isosceles triangular sub-electrode 6; however, electrical lead connection 20a' is proved on the side 10a' at which corner points 31 and 33 of two sub-electrodes 4 and 8, respectively, are located. Corner points 31 and 33 are connected to connecting leads 24 and 28, respectively. A middle terminal 29 on the side of a middle sub-electrode 6 turned toward the side 10a', is attached to connecting lead 26. Thus, as will be noted, connecting leads of equal length, 24 and 28, are attached to the two outer sub-electrodes 4 and 8. The higher impedance of connecting lead 26 can be compensated for in the related monitoring circuitry. But here again, it is noted that a partial peeling or lifting of electrode 2 can be immediately and dependably detected since a surface area inequality results upon peeling.

Figure 4:
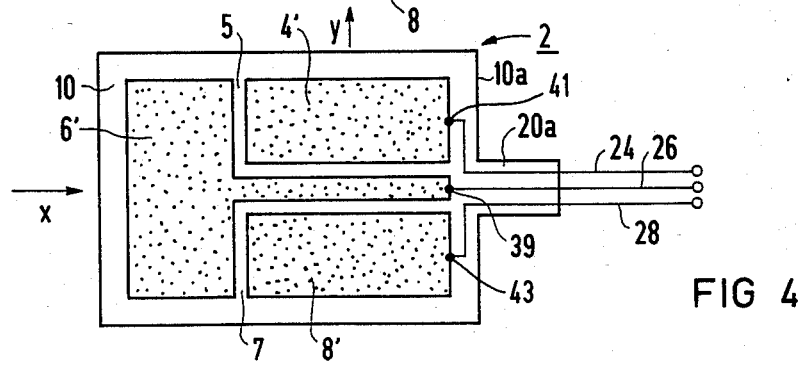
FIG. 4 illustrates a further three-element neutral electrode with three essentially rectangular sub-electrodes formed into a T-shape.

In the construction shown in FIG. 4, essentially the same reference symbols are used as in FIGS. 1 through 3. Here, three sub-electrodes 4', 6' and 8' are provided which are essentially rectangular in shape. Sub-electrodes 4' and 8' are arranged in juxtaposition in a direction y that is perpendicular to the given x-direction. The additional sub-electrode 6' is formed in a T-shape so that the narrow foot of the T lies between the two sub-electrodes 4' and 8' while forming insulating strips 5 and 7. At least the two outer sub-electrodes 4' and 8' are designed to have equal surface areas and the T-shaped sub-electrode 6' may have a surface area equal to the sum of the surface areas of sub-electrodes 4' and 8'. The lead routing is such that connecting lead 26 is joined with a connecting point 39 at the foot of sub-electrode 6'. The two other connecting leads 24 and 28 are routed to connecting points 41 and 43 adjacent to the side 10a. Thus, the three connecting points 39, 41 and 43 lie close together on a single line parallel to the y-direction.

Thus, there has been shown and described a novel neutral electrode which fulfills all the objects and advantages sought therefore. Many changes, modifications, variations and other uses and applications of the subject invention will, however, become apparent to those skilled in the art after considering this specification and the accompanying drawings which disclose preferred embodiments thereof. For example, in contrast to the presentation in FIG. 4, it may be preferable to have all three connecting points 39, 41 and 43 even closer together so that the three corresponding connecting leads 24, 26 and 28 can run parallel to each other and be of equal length. This also applies to FIGS. 1 and 2. In this configuration too, the advantage results that no additional impedances occur that would have to be compensated for in the monitoring circuit. Here too, the equal length of connecting leads 24, 26 and 28 offer an advantage in fabrication. And again, the construction shown with an essentially rectangular contact surface, assures that a separation or peeling is dependably and rapidly detected. All such changes, modifications, variations and other uses and applications which do not depart from the spirit and scope of the invention are deemed to be covered by the invention which is limited only by the claims which follow.

We claim:

1. An electrode useful as a neutral electrode for connection via electrical lines to an HF-surgical instrument, said electrode being of the type including three partial electrodes extending in a given direction and arranged alongside one another on a common carrier which is essentially rectangular in the given direction, wherein:

one of said partial electrodes is T-shaped, having head and foot portions, and arranged centrally on the carrier with the foot portion extending on the carrier in the given direction;

two other of said partial electrodes are essentially of rectangular shape and equal surface area and are arranged on the carrier so as to interpose in the given direction the foot portion of the T-shaped partial electrode and form insulating strips between said foot portion and said two other partial electrodes; and the electrical line connections are provided for each of the three partial electrodes, one at an end of the foot portion which faces away from the head portion of the T-shaped partial electrode and the other two electrical line connections are at adjacent ends of the two other partial electrodes which also face away from the head portion of the T-shaped partial electrode.

2. An electrode according to claim 1, wherein said T-shaped partial electrode is formed with the same surface area as the sum of the surface areas of the two other of said partial electrodes.

* * * * *